(12) United States Patent
Simas, Jr. et al.

(10) Patent No.: US 6,997,916 B2
(45) Date of Patent: Feb. 14, 2006

(54) FLUID TRANSFER HOLDER ASSEMBLY AND A METHOD OF FLUID TRANSFER

(75) Inventors: Robert Simas, Jr., Keene, NH (US); David MacLean, Swanzey, NH (US)

(73) Assignee: Smiths Medical ASD, Inc., Keene, NH (US)

( * ) Notice: Subject to any disclaimer, the term of this patent is extended or adjusted under 35 U.S.C. 154(b) by 0 days.

(21) Appl. No.: 10/749,514

(22) Filed: Jan. 2, 2004

(65) Prior Publication Data
US 2005/0148992 A1    Jul. 7, 2005

(51) Int. Cl.
*A61B 19/00*    (2006.01)

(52) U.S. Cl. ............... 604/411; 604/403; 604/414; 604/905

(58) Field of Classification Search ........... 222/80–82, 222/89–91, 541.1–541.2, 544–546, 562; 220/200, 202, 203.01, 203, 253, 255, 255.1, 220/258.1, 258.3–258.4, 265–268, DIG. 34; 206/0.5, 216; 604/403, 411–416, 903, 905; 128/DIG. 26, 912; 600/573, 575–579; 215/10, 215/14, 17, 26–30, 40, 43, 44, 200, 227, 215/272–73, 277, 216–7, 324, DIG. 3
See application file for complete search history.

(56) References Cited

U.S. PATENT DOCUMENTS

| | | | |
|---|---|---|---|
| 4,296,786 A * | 10/1981 | Brignola | ............ 141/309 |
| 5,344,417 A | 9/1994 | Wadsworth, Jr. | |
| 5,360,423 A | 11/1994 | McCormick | |
| 5,374,264 A | 12/1994 | Wadsworth, Jr. | |
| 5,536,262 A * | 7/1996 | Velasquez | ............ 604/533 |
| 5,879,345 A * | 3/1999 | Aneas | ............ 604/411 |
| 5,893,397 A | 4/1999 | Peterson et al. | |
| 6,601,721 B1 * | 8/2003 | Jansen et al. | ............ 215/249 |
| 6,875,204 B1 * | 4/2005 | Hopkins et al. | ............ 604/414 |
| 2004/0215106 A1 * | 10/2004 | Sampson et al. | ............ 600/576 |

* cited by examiner

*Primary Examiner*—Patricia Bianco
(74) *Attorney, Agent, or Firm*—Louis Woo

(57) ABSTRACT

A fluid transfer system has a holder that is made of a cylindrical member having a closed end and an open end. The closed end has fitted thereto a luer and a cannula that extends into the interior of the holder. The holder has a distal portion that has a first cross section and a proximal portion that has a second cross section. The cross section of the distal portion is smaller than the cross section of the proximal portion. The distal and proximal portions are joined by a shoulder. The fluid transfer system also includes an adapter that is inserted to the holder from the open end of the holder. The adapter has a base having a central opening and a cylindrical tube that extends from the central opening. The diameter of the cylindrical tube is slightly smaller than the diameter of the distal portion and is configured to accept a first type of fluid collection store such as a vacuum tube. With the adapter removed, the holder can accept a differently dimensioned fluid collection store such as for example a blood culture collection bottle.

14 Claims, 2 Drawing Sheets

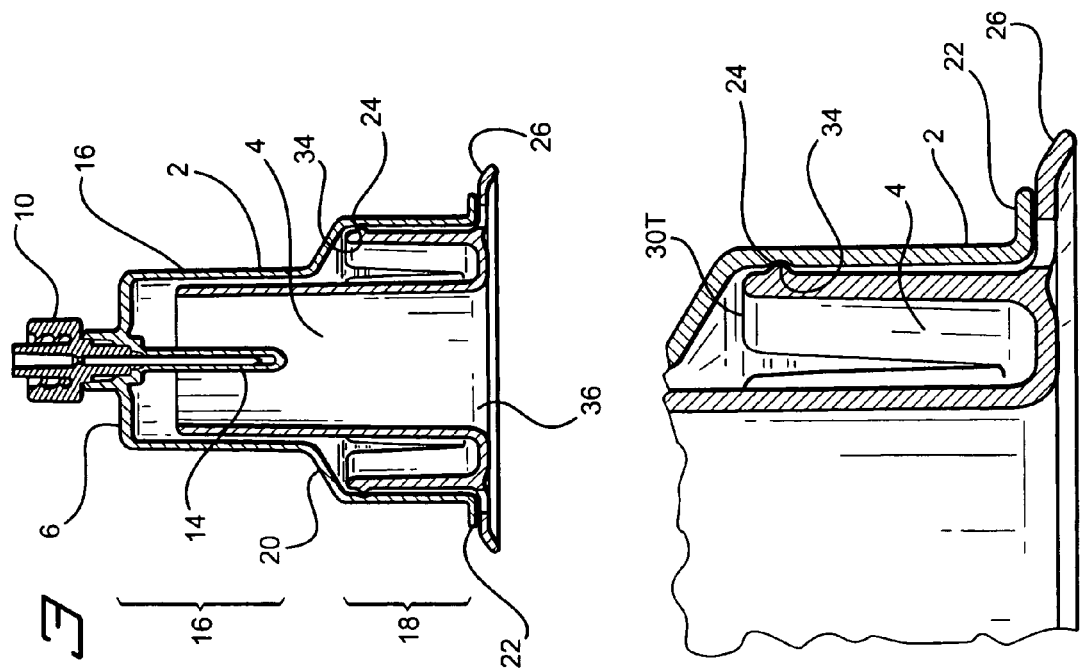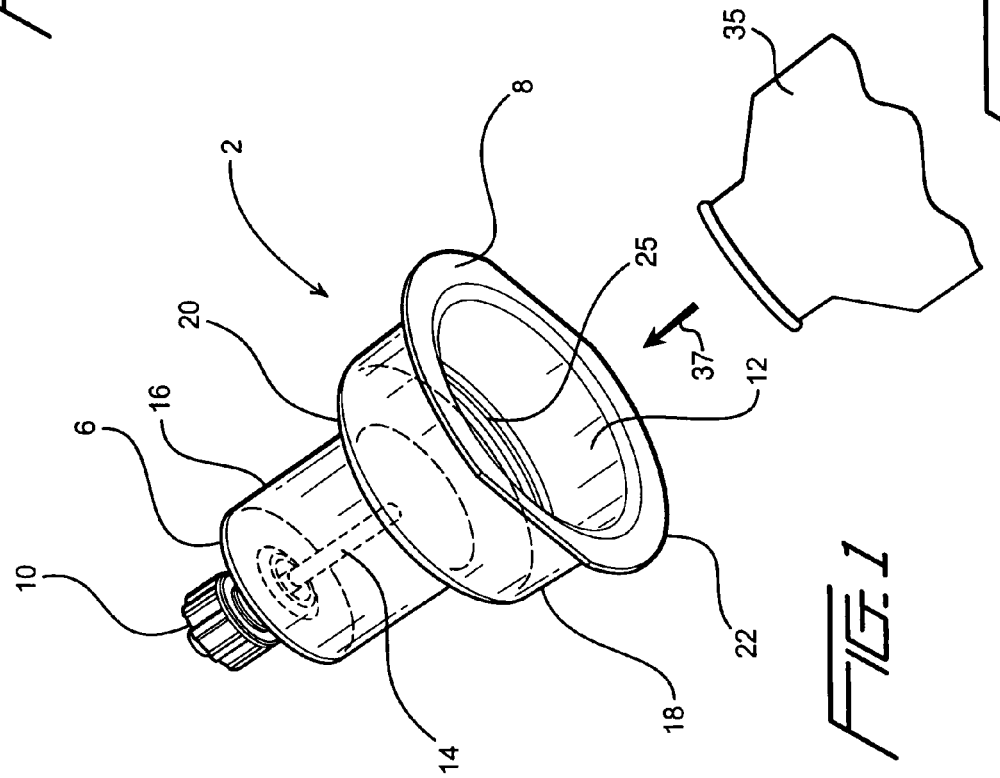

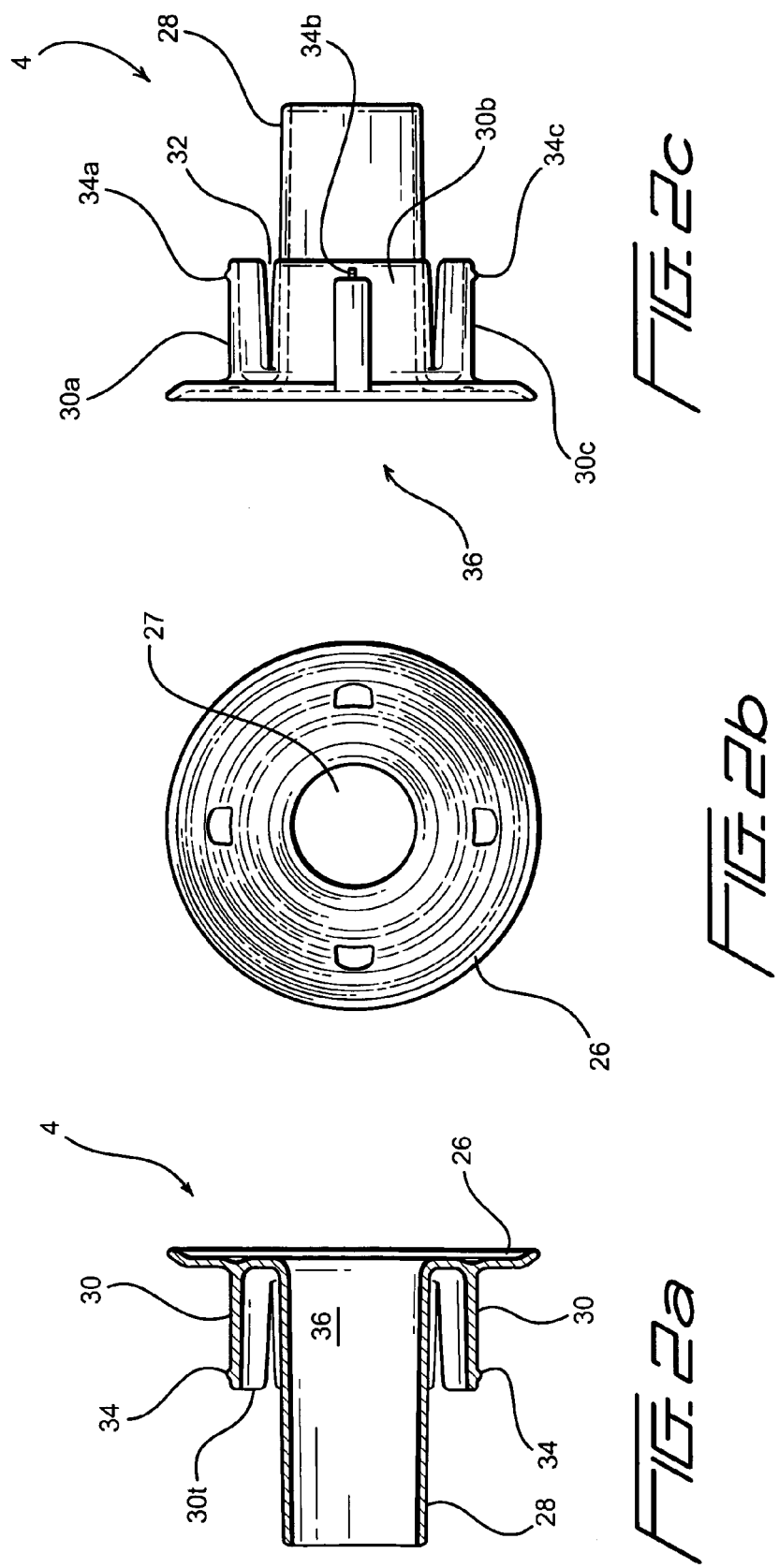

FLUID TRANSFER HOLDER ASSEMBLY AND A METHOD OF FLUID TRANSFER

FIELD OF THE INVENTION

The instant invention relates to the collection of biological fluid specimens and particularly the collection of bodily fluids such as for example blood from a patient and the transfer of the bodily fluid from the patient to differently dimensioned fluid storage bottles or tubes.

BACKGROUND OF THE INVENTION

The bodily fluid from a patient, for example blood, is usually withdrawn from a patient and stored in either a vacuum tube or a blood culture collection bottle. To collect blood into a vacuum tube, conventionally a Vacutainer holder into which a vacuum tube may be inserted is used. In particular, a double-ended needle is threadingly mated to the Vacutainer holder, the patient is pricked with the end of the needle that extends from the Vacutainer holder, after which a vacuum tube is inserted to the Vacutainer holder so that its closure rubber stopper is pierced by the other of the double-ended needle. Blood from the vein of the patient then flows into and is collected within the vacuum tube. In the instance where the blood of the patient is to be collected in a blood culture collection bottle, an intravenous needle is inserted to the vein of the patient after it is connected to a holder to which the blood culture bottle may be mated. Examples of such holders are given in U.S. Pat. Nos. 5,344,417 and 5,374,264. Such holders prevent potential accidental needle pricks by the contaminated needles to the user.

The prior art also discloses the use of a collection device for transferring bodily fluids to a blood specimen tube and a blood collection bottle. Prior art U.S. Pat. No. 5,360,423 teaches the use of a cap that covers the open end of a collection cup, with a smaller central opening provided at the center of the cap through which a blood collection tube may be inserted. The problem of the '425 prior art device is that the only thing that guides the insertion of the tube to the collection cup is the circumferential lip of the central opening of the cap through which the vacuum tube passes. As a consequence, the insertion of the blood collection tube to the collection cup may be off axially, resulting in the rubber stopper that covers the blood collection tube being pierced at an off-centered location. Moreover, there is nothing to support the portion of the blood collection tube that has passed through the central opening of the cap, before the rubber stopper is pierced by the cannula inside the collection cup.

SUMMARY OF THE INVENTION

The present invention fluid transfer safety holder has a cylindrical cup-shaped member that has a distal portion extending from a closed end and a proximal portion extending from an open end. The distal and proximal portions are joined by a shoulder that extends from the smaller diametered distal portion to the larger diametered proximal portion. The diameter of the distal portion is dimensioned such that it allows the mating thereto of a conventional vacuum tube. The dimension of the proximal portion is such that it allows the insertion thereto of a portion of the body of a blood culture collection bottle.

At the closed end of the cylindrical member there is fitted a luer that allows the cylindrical member to be connected to a corresponding luer of a syringe that may have contained therein fluid withdrawn from the patient. Alternatively, the luer may be connected to an intravenous needle that may be inserted in the vein of the patient. The luer end has extending therefrom into the interior of the cylindrical member at its distal portion a cannula that pierce the rubber stopper of a vacuum tube, or the cover at the neck of a blood culture collection bottle, when either one is inserted to the distal portion of the cup-shaped member.

The fluid transfer safety holder further includes an adapter that has a base with a central opening and a cylindrical tube that extends from the base for extending the opening. The cylindrical tube has a diameter that is slightly smaller than that of the distal portion, so that the former may be inserted to the latter. A non-continuous cylindrical wall extends from the base of the adapter for circumferentially surrounding a portion of the cylindrical tube. The height or length of the wall is such that it substantially matches the distance of the proximal portion, so that when the adapter is inserted to the cylindrical member, only the cylindrical tube is inserted to the distal portion.

The non-continuous wall is made of adjacent sections. The diameter of the circumferential wall is such that it is slightly smaller than the diameter of the proximal portion of the holder. At each section of the wall there is formed a protuberance at its exterior. These protuberances, or fingers, will mate to a groove that is formed at the inner surface of the proximal portion of the cylindrical member, when the adapter is fitted to the member. With the protuberances mated to the internal groove, the adapter and the member are prevented from being inadvertently disengaged from each other, once the adapter is inserted to the member.

The opening at the base of the adapter, which extends along the length of the tube extending from the base, is dimensioned to accept a conventional vacuum tube, so that once the adapter is fitted into the member, a passage is provided by the adapter for guiding a vacuum tube to the safety holder. With the guiding support of the adapter tube, the vacuum tube is ensured to be inserted to the safety holder axially, so that its rubber stopper would be pierced at substantially its center by the cannula in the holder member.

For transferring fluid to a blood culture collection bottle, the adapter is removed and the blood culture collection bottle is inserted to the cup-shaped member, with the neck of the bottle being inserted to the distal portion while the front portion of the bottle rests within the proximal portion of the member.

BRIEF DESCRIPTION OF THE FIGURES

The present invention will become apparent and the invention itself will be best understood with reference to the following description of an embodiment of the invention taken in conjunction with the accompanying drawings, wherein:

FIG. 1 is a perspective view of the cylindrical member of the fluid transfer safety holder of the instant invention;

FIGS. 2a, 2b and 2c are respective cross-sectional side view, back view and side view of the adapter of the fluid transfer safety holder of the instant invention;

FIG. 3 is a cut away side view of the fluid transfer safety holder of the instant invention showing the adapter having been mated to the holder member; and FIG. 4 is an enlarged view of the circled section of FIG. 3.

DETAILED DESCRIPTION OF THE INVENTION

With reference to FIGS. 1 and 2a–2c, the fluid transfer system of the instant invention is shown to include a holder member 2 and an adapter member 4. Holder member 2 is a cylindrical member having a closed end 6 and an open end 8. Closed end 6 is fitted with a luer 10 that is matable with a luer of a syringe or an intravenous needle, as is well known in the art. Open end 8 has an opening 12 through which adapter member 4 may be inserted to the interior of holder member 2. A cannula or needle 14, shown covered by a rubber boot or shroud, extends into the interior of holder member 2 for establishing a fluid pathway from luer 10 to the interior of holder member 2.

Holder member 2 comprises a distal portion 16 and a proximal portion 18. Distal portion 16 has a diameter or cross section that is smaller than the diameter or cross section of proximal portion 18. As best shown in FIG. 3, distal portion 16 is joined to proximal portion 18 by a shoulder 20 that slopes from distal portion 16 to proximal portion 18, as a result of the difference in the respective diameters of distal portion 16 and proximal portion 18.

An end flange 22 extends circumferentially from opening 12 at the open end 8 of proximal portion 18. As best shown in FIG. 4, a circumferential groove 24 is formed at the internal surface of proximal portion 18, at a location thereof that is close to the junction where proximal portion 18 joins distal portion 16 via shoulder 20.

The adapter of the fluid transfer system has a base 26 with an opening 27. A cylindrical tube 28 extends from the central opening to a length that enables a distal part of it to be fitted into distal portion 16, when adapter 4 is inserted to holder member 2. There is circumferentially surrounding another part of tube 28 a non-continuous wall 30 made of a number of adjacent sections 30a–30d. The discontinuity of wall 30 stems from the slots 32 that are formed between the adjacent sections of wall 30 for providing the sections of wall 30 with the characteristics of being pushed in or squeezed together ever so slightly, when adapter 4 is inserted to holder 2.

At each of the sections 30a–30d of wall 30, at a location proximal to its top, there is formed a protuberance or a finger 34a–34d. It should be noted that wall section 30d as well as its protuberance 34d are not shown, since that wall section is located away from the view as shown in FIG. 2c. As best shown in FIGS. 3 and 4, when adapter 4 is fully inserted to holder member 2, protuberances 34 would mate with groove 24 to thereby lockingly maintain adapter 4 to holder 2 so as to prevent the holder and the adapter from inadvertently disengaging from each other. The respective geometries of the protuberances 34 and groove 24 are such that with a predefined force, adapter 4 may be readily removed from holder 2.

The height of wall 30 is such that the top of wall 30, designated 30t in FIG. 4, would be approximately the height of proximal portion 18 when adapter 4 is fully inserted to holder 2. Flange 22 provides a stop against base 26 of adapter 4 to prevent adapter 4 from being pushed further into the interior of holder 2, and to ensure that protuberances 34 would snap into groove 24 and not go any further.

The diameter of cylindrical tube 28 is slightly smaller than the diameter of distal portion 16, so that tube 28 could be readily fitted into distal portion 16, as shown in FIG. 3. Similarly, the diameter of wall 30 is configured such that it is slightly smaller than the diameter of proximal portion 18, i.e., opening 12 at the open end 8 of holder 2. As shown in FIG. 2a, the diameter or cross section of tube 28, or the opening of adapter 4, is designated 36. Opening 36 of adapter 4 is smaller than opening 25 of holder 2, and is designed to have a cross-section slightly larger than the cross-section of a fluid collection store of a first dimension, such as for example a conventional vacuum tube. The opening 12 of holder 2, on the other hand, is sized to accept the body of a differently dimensioned fluid collection store, for example a blood culture collection bottle made by the Biomerieux company. The blood culture collection bottle has a neck that is dimensioned to fit into the opening provided by distal portion 16.

When the fluid transfer system of the instant invention is assembled as shown in FIG. 3, a conventional vacuum tube may be inserted through opening 36 of adapter 4, so as to be guided by cylindrical tube 28 into distal portion 16, so that its rubber stopper may be pierced by cannula 14. Once pierced, a fluid path is created from luer 10 into the interior of the vacuum tube. Although not shown, a syringe may be mated to luer 10 by its own luer, as is well known. In which case the fluid stored in the syringe may be transferred to the vacuum tube.

An intravenous needle with a luer connector may also be mated with luer 10 of the fluid transfer system of the instant invention. The intravenous needle may be inserted to the vein of the patient so that the blood of the patient may be withdrawn into the vacuum tube fitted into the safety holder system of the instant invention.

Instead of a vacuum tube, if it is desired to collect blood from a patient or from a reservoir, adapter 4 may be removed from holder 2 by the application of a predetermined force. Once adapter 4 is removed, holder 2, as best shown in FIG. 1, may accept the aforementioned blood culture collection bottle. In particular, the bottle, designated 35 in FIG. 1, is inserted through opening 12 into holder 2 in the direction per directional arrow 37, with the neck of the bottle inserting to distal portion 16 while a part of the bottle proper being inserted to proximal portion 18. Shoulder 20 in this case provides the stop for the bottle. As is well known, such blood culture collection bottle also has a rubber stopper, or some other seal, that covers its neck so that once the bottle is inserted to holder 2, the rubber stopper would be punctured by cannula 14 to establish a fluid path from luer 10 to the interior of the blood culture collection bottle. The bodily fluid of the patient such as for example blood is then collected in the blood culture collection bottle.

What is claimed is:

1. A fluid transfer system, comprising:

a cylindrical member having a closed end and an open end, said closed end fitted with a luer for connection to a fluid store or an intravenous needle, a cannula extending from said luer into said member to effect a fluid conduit with said luer, said member having a distal portion of a first diameter that extends from said closed end and a proximal portion of a second diameter that extends from said open end, said second diameter being larger than said first diameter, said first diameter being sized to accept a vacuum tube and said second diameter being sized to accept the neck and a portion of a fluid collection bottle;

an adapter fittable into said member by insertion from said open end, said adapter having a base with a central opening, a cylindrical tube extending from said base in communication with said opening, said tube having a diameter slightly smaller than said first diameter and a part fittable partially into said distal portion of said member to provide a passage wherethrough a vacuum tube may be guided into said member to be pierced by said cannula so that a fluid communications path may be effected from said luer to the interior of the vacuum tube, said adapter having a noncontinuous circular wall having a cross-section smaller than said second diameter formed by adjacent sections extending from said base to encircle another part of said cylindrical tube that is not fitted into said distal portion of said member, the height of said wall substantially equaled to the length of said proximal portion.

2. Fluid transfer system of claim 1, further comprising a circumferential groove formed along the inside surface of said proximal portion of said cylindrical member and protuberances each formed externally at a section of said wall of said adapter, wherein when said adapter is inserted to member, said protuberances of said adapter mate with said groove at said member to prevent said adapter from being inadvertently disengaged from said member.

3. Fluid transfer system of claim 1, wherein said member has a flange extending substantially circumferentially about said open end, said flange acting against said base of said adapter to prevent said adapter from being pushed further into said member when said adapter is inserted into said member.

4. Fluid transfer system of claim 1, wherein a shoulder is formed at said member where said distal portion joins said proximal portion, said shoulder guiding said cylindrical tube of said adapter into said distal portion of said member when said adapter is inserted into said member.

5. A safety holder for transferring fluid from either a syringe or a patient to different dimensioned fluid collection stores, comprising:
   a cylindrical member having a closed end and an open end, said closed end fitted with a luer for connection to the syringe or an intravenous needle for insertion to the patient, a cannula extending from said luer into said member to effect a fluid conduit with said luer, said member having a distal portion and a proximal portion, said distal portion extending from said closed end and having a first diameter sized to accept a first fluid collection store, said proximal portion extending from said open end and having a second diameter sized to accept a second fluid collection store;
   an adapter matable to said member by insertion from said open end, said adapter having a base with a central opening, a cylindrical tube extending from said base in communication with said opening, said tube having a diameter slightly smaller than said first diameter and a part fittable partially into said distal portion of said member to provide a passage wherethrough said first fluid collection store may be extended into said member to be pierced by said cannula, said adapter having a noncontinuous circular wall having a cross section smaller than said second diameter formed by adjacent sections extending from said base to encircle another part of said cylindrical tube not to be fitted into said distal member of said member, the height of said wall substantially equaled to the length of said proximal portion;
   wherein said second fluid collection store is fittable to said proximal portion of said member when said adapter is not mated to said member.

6. Safety holder of claim 5, wherein said second diameter is larger than said first diameter.

7. Safety holder of claim 5, further comprising a circumferential groove formed along the inside surface of said proximal portion of said cylindrical member proximate to the intersection of said distal and proximal portions, protuberances each formed externally at a section of said wall of said adapter, said protuberances mating with said groove to prevent said adapter from being inadvertently disengaged from said member when said adapter is inserted to said member.

8. Safety holder of claim 5, wherein said member has a flange extending substantially circumferentially about said open end, said flange acting against said base of adapter to prevent said adapter from being pushed further into said member when said adapter is inserted into said member.

9. Safety holder of claim 5, wherein a shoulder is formed at said member for joining said distal portion to said proximal portion, said shoulder guiding said cylindrical tube of said adapter into said distal portion of said member when said adapter is inserted into said member.

10. A method of establishing a fluid path between fluid stores and a luer connection, comprising the steps of:
   a) providing a cylindrical member having a closed end, an open end, a distal portion and a proximal portion, said distal portion extending from said closed end and having a first diameter sized to accept a first fluid collection store, said proximal portion extending from said open end and having a second diameter sized to accept a second fluid collection store, said second diameter being larger than said first diameter;
   b) fitting a luer to said closed end for connection to the syringe or an intravenous needle for insertion to the patient;
   c) connecting a cannula from said luer into said member to effect a fluid conduit with said luer;
   d) providing an adapter having a base with a central opening, a cylindrical tube extending from said base in communication with said opening, said tube having a diameter slightly smaller than said first diameter and a part fittable partially into said distal portion of said member, a noncontinuous circular wall formed by adjacent sections extending from said base to encircle another part of said cylindrical tube not fittable into said distal portion of said cylindrical member, the height of said wall substantially equaled to the length of said proximal portion and the cross section of said wall being smaller than said second diameter; and
   e) inserting said adapter into said member to establish a passage wherethrough said first fluid collection store may be guided into said member to be pierced by said cannula.

11. Method of claim 10, further comprising the steps of:
   removing said adapter from said member; and
   fitting said second fluid collection store to said proximal portion of said member so that the neck of said second fluid collection store is fitted into said distal portion while a part of its main body is fitted within said proximal portion to establish a fluid path from said luer to the interior of said second fluid collection store.

12. Method of claim 10, further comprising the steps of:
   forming a circumferential groove along the inside surface of said proximal portion of said cylindrical member proximate to the intersection of said distal and proximal portions;
   forming a plurality of protuberances each externally at a section of said wall of said adapter;
   wherein said protuberances mate with said groove to prevent said adapter from being inadvertently disen gaged from said member when said adapter is inserted to said member.

13. Method of claim 10, wherein said step a comprises the step of:
extending a flange substantially circumferentially about said open end of said member, said flange acting against said base of said adapter to prevent said adapter from being pushed further into said member when said adapter is inserted into said member.

14. Method of claim 10, wherein said step d comprises the step of:
forming a shoulder at said member for joining said distal portion to said proximal portion, said shoulder guiding said cylindrical tube of said adapter into said distal portion of said member when said adapter is inserted into said member.

* * * * *